United States Patent [19]

Wolgemuth et al.

[11] Patent Number: 4,831,019

[45] Date of Patent: May 16, 1989

[54] PHARMACEUTICAL PREPARATIONS OF 4-DEMETHOXY-N-TRIFLUOROACETYL ANTHRACYCLINES

[75] Inventors: Richard L. Wolgemuth, Plain City; John P. Carter, Columbus, both of Ohio

[73] Assignee: Adria Laboratories, Inc., Dublin, Ohio

[21] Appl. No.: 736,871

[22] Filed: May 22, 1985

Related U.S. Application Data

[63] Continuation of Ser. No. 547,518, Oct. 31, 1983, abandoned.

[51] Int. Cl.$^4$ .............................................. A61K 31/70
[52] U.S. Cl. .................................................... 514/34
[58] Field of Search ...................... 536/6.4; 514/27, 34

[56] References Cited

U.S. PATENT DOCUMENTS

| 4,077,988 | 3/1978 | Arcamone et al. | 536/6.4 |
| 4,107,423 | 8/1978 | Arcamone et al. | 536/6.4 |
| 4,125,607 | 11/1978 | Arcamone et al. | 536/6.4 |

OTHER PUBLICATIONS

Johnson et al. Cancer Treatment Reviews (1975), 2 pp. 1-31.

Primary Examiner—Johnnie R. Brown
Assistant Examiner—Elli Peselev
Attorney, Agent, or Firm—Smith & Schnacke

[57] ABSTRACT

Antineoplastic pharmaceutical preparations and a method for treating neoplastic conditions using 4-demethoxy-N-trifluoroacetyldaunomycin and 4-demethoxy-N-trifluoroacetyldoxorubicin.

1 Claim, No Drawings

PHARMACEUTICAL PREPARATIONS OF 4-DEMETHOXY-N-TRIFLUOROACETYL ANTHRACYCLINES

This is a continuation of application Ser. No. 547,518, filed Oct. 31, 1983, now abandoned.

BACKGROUND OF THE INVENTION

The present invention relates to a pharmaceutical preparation for treating neoplastic conditions, and particularly myeloblastic leukemia.

A variety of antineoplastic agents have been used in the chemotherapeutic treatment of leukemias in humans. Doxorubicin and daunomycin are generally recognized as two of the most effective agents against these diseases. It is postulated that these compounds function by inserting into the DNA complex and thereby prevent replication and division of the neoplasm. Doxorubicin hydrochloride is available from Adria Laboratories, Inc. under the tradename Adriamycin and has been approved for use by the Food and Drug Administration. Specifically, doxorubicin and daunomycin have the formula:

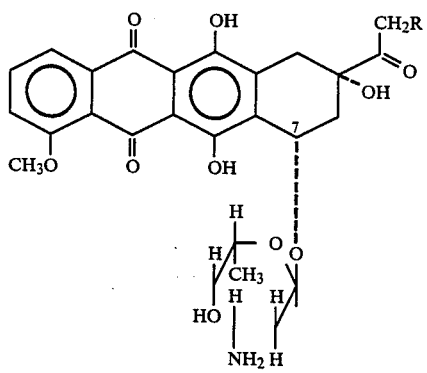

with the compound being doxorubicin when R is —OH and daunomycin when R is —H.

Unfortunately, repeated use of doxorubicin and daunomycin is restricted by acute dose-limiting myelosuppression and by chronically dose-limiting cardiotoxicity. Consequently, efforts have been directed to developing more active antineoplastic agents which have fewer of these side effects. The compound of choice would not produce these side effects and would be suitable for frequent administration. Ideally, the compound would also be orally active so that it could be easily administered outside of the hospital setting, possibly by the patient himself.

Many of the efforts to develop preferred antineoplastic agents have centered around derivatives of doxorubicin and daunomycin. Two derivaties which have been found to be more active than their natural analogues are 4-demethoxydaunomycin and 4-demethoxydoxorubicin. These compounds are reported in U.K. Pats. Nos. 1,511,680 and 1,500,421 or 1978. 4-Demethoxydaunorubicin is orally active but highly myelosuppressive. 4-Demethoxydoxorubicin is only modestly potent and is myelosuppressive and orally active.

There are few instances in the literature where N-trifluoroacetyl derivatives of daunomycin or doxorubicin are disclosed as being useful antineoplastic agents. U.S. Pat. No. 4,035,566 to Israel et al discloses pharmaceutical preparations containing N-trifluoroacetyl derivatives of doxorubicin-14-alkanoates and daunomycin-14-alkanoates, but the compounds are not disclosed as being orally active.

Accordingly, there is a need for an orally active antineoplastic agent that is highly active and suitable for frequent administration.

SUMMARY OF THE INVENTION

The present invention is based on applicants' discovery that 4-demethoxy-N-trifluoroacetyldaunomycin and 4-demethoxy-N-trifluoroacetyldoxorubicin are orally active and exhibit activity far greater than 4-demethoxydoxorubicin, or 4-demethoxydaunorubicin. While the N-trifluoroacetyl derivatives of 4-demethoxydoxorubicin and 40-demethoxydaunomycin are known as intermediates in the synthesis of other doxorubicin and daunomycin derivatives, their effectiveness in pharmaceutical preparations as antineoplastic agents and as antineoplastic agents suitable for oral administration, has not been known.

Accordingly, the present invention provides antineoplastic pharmaceutical preparations which comprise a therapeutically effective amount of 4-demethoxy-N-trifluoroacetyldaunomycin or 4-demethoxy-N-trifluoroacetyldoxorubicin and a pharmaceutically acceptable non-toxic carrier.

In addition, the present invention provides a method for treating leukemia and other neoplastic conditions comprising administering therapeutically effective amounts of 4-demethoxy-N-trifluoroacetyldaunomycin or 4-demethoxy-N-trifluoroacetyldoxorubicin to a patient suffering from such a condition.

In accordance with the preferred embodiments of the present invention, the pharmaceutical preparations of the present invention are constituted for oral administration.

DETAILED DESCRIPTION OF THE INVENTION

The pharmaceutical preparations of the present invention can be formulated for the desired mode of administration by dispersing or dissolving the compounds in the appropriate non-toxic, pharmaceutically acceptable carrier.

The compounds can be administered parenterally (e.g., by intraperitoneal injection), but are particularly advantageous for oral administration. Suitable carriers for the compounds include dimethyl sulfoxide, propylene glycol, glycerol, peanut oil, and a 10% by volume aqueous solution of sorbitan monooleate. Aqueous media are preferably buffered to pH 7.2–7.5, the physiological range, using conventional buffers. If desired, saline solution can be used.

The compounds of the present invention have been shown to be useful in treating P-388 leukemia, but it is foreseeable that the compounds will be useful in treating various other neoplastic conditions including acute myeloblastic and lymphoblastic leukemias, Hodgkins disease, ovarian cancer, and others, The P-388 lymphocytic leukemia model is the principal screen used by the National Cancer Institute for screening compounds against animal tumors.

The compounds used in the present invention have been found to have a much higher therapeutic ratio (T/C) than either daunorubicin or 4-demethoxydaunorubicin. Consequently, it is anticipated that these compounds can be administered at higher dosages and more frequently than daunomycin and doxorubicin. A suitable dosage for the compounds is believed to lie in the range of about 30 to 750 mg/m$^2$ with optimum dosages expected to lie in the range of about 200 to 500 mg/m$^2$.

There are several syntheses that can be used to prepare 4-demethoxy-N-trifluoroacetyldaunorubicin and 4-demethoxy-N-trifluoroacetyldoxorubicin reported in the literature. Reference can be made to U.K. Pat. No. 1,509,875, for the preparation of 4-demethoxy-N-trifluoroacetyldaunomycin. Alternatively, the syntheses illustrated in the following examples may be used.

EXAMPLE 1

4-Demethoxy-N-trifluoroacetyldaunomycin

4-Demethoxydaunomycin hydrochloride (0.564 gram, 0.001 mole) was dissolved in 5 ml of anhydrous methanol and cooled to 0° C. Then 1.0 ml of a 1.0 M solution of sodium methoxide in methanol was slowly added. The mixture was allowed to stand at 0° C. for 10 minutes and 0.4 ml of S-ethyl thiotrifluoroacetate was added and the mixture stirred overnight. After sixteen hours, an additional 0.18 ml of 1.0M sodium methoxide in methanol was added, and the mixture stirred for two hours. The solvent was then removed under reduced pressure and the residue partitioned between 0.5M aqueous citric acid and methylene chloride. The organic layer was separated, dried over Na$_2$SO$_4$ and the solvent removed to give 0.52 grams of a red solid on thin layer homogeneous chromatography (SiO$_2$; 5% methanol in methylene chloride).

The sample was analyzed by high pressure liquid chromatography, using a Microbondapak C-18 column with a mobile phase mixture of 33% acetonitrile/33% methanol/33% water/0.1% H$_3$PO$_4$ at a flow rate of 1.5 ml per minute with UV detection at 254 nm. The sample was shown to contain a compound (94% by area) eluting in ten minutes.

A 300 mHz nuclear magnetic resonance spectrum was obtained of the sample. It was found to be consistent with the proposed structure.

EXAMPLE 2

4-Demethoxy-N-trifluoroacetyldoxorubicin

The following procedure is suggested for the synthesis of the title compound. Proceeding as in Example 1, 4-demethoxydoxorubicin is reacted with methanolic sodium methoxide and S-ethyl thiotrifluoroacetate. Following the reaction the isolated and product is purified to afford 4-demethoxy-N-trifluoroacetyldoxorubicin.

To illustrate the improved activity of the compounds of the present invention, 4-demethoxy-N-trifluoroacetyldaunomycin was tested in comparison to 4-demethoxydaunomycin in the murine P-388 leukemia screen according to standard National Cancer Institute protocols as set forth in Example 3.

EXAMPLE 3

Female CDF1 mice and female DBA2 mice were obtained from Laboratory Animal Supply Company, Indianapolis, Ind. They were housed in gang stainless steel cages in environmentally controlled animal facilities and fed Purina Laboratory Chow. Water and food were available ad libitum and all mice were allowed at least 1 week for adaptation to their surroundings before they were assigned to a study.

The tumor was maintained by continuous passage in the DBA2 mice. On Day 0, ascitic fluid was removed from a DBA2 mouse, diluted with Hank's balanced salt solution, counted on a Coulter counter (Model MHR) and implanted intraperitoneally (0.2 ml) in CDF1 mice. Twenty-four hours later, mice were randomly distributed into treatment groups and administered drug orally in a total volume of 0.2 ml on a day 1, 5 and 9 schedule. Each group of mice was observed daily for 30 days.

Median survival time (MST) and therapeutic ratio (T/C) for 4-demethoxy-N-trifluoroacetyldaunomycin (Compound A) and 4-demethoxydaunomycin (Compound B) are shown in the Table below.

TABLE

| Dosage (mg/kg) | A MST (days) | B MST (days) | A T/C | B T/C |
| --- | --- | --- | --- | --- |
| 1.56 | — | 11 | — | 118 |
| 3./2 | 9 | 14 | 102 | 156 |
| 6.25 | 10 | 12 | 108 | 126 |
| 12.50 | 9 | — | 102 | — |
| 25.0 | 15 | — | 161 | — |
| 50.0 | 26 | — | 285 | — |

Saline Control MST=9.83

Cremphor Control MST=9.30

Having described the invention in detail and by reference to specific embodiments thereof, it will be apparent that numerous variations are possible without departing from the spirit and scope of the following claims.

What is claimed is:

1. A method for treating neoplastic conditions which comprises:
   orally administering to a patient suffering from such a condition a pharmaceutical preparation containing a therapeutically effective amount of the compound 4-demethoxy-N-trifluoroacetyl daunomycin or 4-demethoxy-N-trifluoroacetyl doxorubicin and a pharmaceutically acceptable, non-toxic carrier.

* * * * *